US008933240B2

(12) United States Patent
Tanis et al.

(10) Patent No.: US 8,933,240 B2
(45) Date of Patent: Jan. 13, 2015

(54) SYNTHESIS FOR THIAZOLIDINEDIONE COMPOUNDS

(75) Inventors: Steven P. Tanis, Carlsbad, CA (US); Timothy Parker, Portage, MI (US); Robert C. Gadwood, Portage, MI (US); Gerald D. Artman, III, Schoolcraft, MI (US); James R. Zeller, Scottsdale, AZ (US)

(73) Assignee: Metabolic Solutions Development Company, LLC, Kalamazoo, MI (US)

( * ) Notice: Subject to any disclaimer, the term of this patent is extended or adjusted under 35 U.S.C. 154(b) by 25 days.

(21) Appl. No.: 13/813,516

(22) PCT Filed: Aug. 9, 2011

(86) PCT No.: PCT/US2011/047010
§ 371 (c)(1),
(2), (4) Date: Apr. 11, 2013

(87) PCT Pub. No.: WO2012/021476
PCT Pub. Date: Feb. 16, 2012

(65) Prior Publication Data
US 2013/0204008 A1 Aug. 8, 2013

Related U.S. Application Data

(60) Provisional application No. 61/372,282, filed on Aug. 10, 2010.

(51) Int. Cl.
C07D 277/34 (2006.01)
C07C 309/65 (2006.01)
C07C 309/66 (2006.01)
C07C 309/73 (2006.01)
C07C 251/48 (2006.01)
C07F 9/145 (2006.01)

(52) U.S. Cl.
CPC ............ C07D 277/34 (2013.01); C07C 309/65 (2013.01); C07C 309/66 (2013.01); C07C 309/73 (2013.01); C07C 251/48 (2013.01); C07F 9/145 (2013.01)
USPC .......................................................... 548/183

(58) Field of Classification Search
USPC .......................................................... 548/183
See application file for complete search history.

(56) References Cited

U.S. PATENT DOCUMENTS

| 4,725,610 A | 2/1988 | Meguro et al. |
| 2003/0027798 A1 | 2/2003 | Druzgala et al. |
| 2007/0004726 A1 | 1/2007 | Biadatti et al. |

FOREIGN PATENT DOCUMENTS

| EP | 0441605 | 8/1991 |
| EP | 0549365 | 6/1993 |
| WO | 92/18501 | 10/1992 |
| WO | 98/57941 | 12/1998 |
| WO | 99/35130 | 7/1999 |
| WO | 03/029251 | 4/2003 |
| WO | 2004/033438 | 4/2004 |
| WO | 02/43807 | 5/2004 |
| WO | 2007/109024 | 9/2007 |
| WO | 2007/109037 | 9/2007 |
| WO | 2008/118327 | 10/2008 |
| WO | 2009/038681 | 3/2009 |
| WO | 2009/148195 | 12/2009 |
| WO | 2011/133441 | 10/2011 |
| WO | 2011/133442 | 10/2011 |
| WO | 2012/021467 | 2/2012 |

OTHER PUBLICATIONS

Colca, et al. Document No. 150:352135 retrieved from CAPLUS, Mar. 27, 2009.*
Chandrasekhar, Sosale, et al., "Effective 'non-aqueous hydrolysis' of oximes with iodic acid in dichloromethane under mild, heterogeneous conditions". Tetrahedron Letters, vol. 43, pp. 4023-4024, Dec. 31, 2002.
Ben-Bassat, Avraham A., et al., "Quaternary Pilocarpine Derivatives as Potential Acetylcholine Antagonist. 2. Alterations in the Lactone and Imidazole Moieties", Journal of Medicinal Chemistry, vol. 19, No. 7, 1976, pp. 928-933.
Bhat, Bashir A., et al., "Synthesis and antihyperglycemic activity profiles of novel thiazolidinedione derivatives", Bioorganic & Medicinal Chemistry, Elsevier, vol. 12, 2004, pp. 5857-5864.
International Search Report for PCT/US2011/032816 dated Jun. 9, 2011.
International Search Report for PCT/US2011/032822 dated Jul. 4, 2011.
International Search Report for PCT/US2011/046992 dated Dec. 19, 2011.
International Search Report for PCT/US2011/047010 dated Oct. 17, 2011.
Kononenko, V. E., et al., "Mannich reaction with 4-azolidones and their analogs", Zhurnal Organicheskoi Khimii, vol. 9, No. 1, 1973, pp. 61-63.
Masaki, Mitsuo, et al., "The Reaction of α-Halo Oximes with Triphenylphosphine. Formation of Imidoyl Bromide and of Oximinophosphine Salts by a Novel Catalytic Effect of Bases", Journal of Organic Chemistry, vol. 32, No. 11, Nov. 1967, pp. 3564-3568.

(Continued)

Primary Examiner — Shawquia Jackson
(74) Attorney, Agent, or Firm — Honigman Miller Schwartz & Cohn LLP; Andrew N. Weber; Jonathan P. O'Brien

(57) ABSTRACT

The present invention provides novel methods for synthesizing PPARγ sparing compounds, e.g., thiazolidinediones, that are useful for preventing and/or treating metabolic disorders such as diabetes, obesity, hypertension, and inflammatory diseases.

47 Claims, No Drawings

(56) References Cited

OTHER PUBLICATIONS

Proposal for the Process Development and Non-GMP Production of a 1 Kg Lot of 2-bromo-1-[5-ethylpyridin-2-yl] ethanone hydrobromide [BEPE] dated Sep. 28, 2011.

Proposal for the Process development and Scale up of 2-bromo-1-[5-ethylpyridin-2-yl]ethanone hydrobromide dated Sep. 26, 2011.

Rakowitz, Dietmar, et al., "In Vitro aldose reductase inhibitory activity of 5-benzyl-1-2,4-thiazolidinediones", Bioorganic & Medicinal Chemistry, Elsevier, vol. 14, 2006, pp. 567-574.

Sohda, Takashi, et al., "Studies on Antidiabetic Agents. II. Synthesis of 5-[4-(1-Methylcyclohexylmethoxy)-benzyl]thiazolidine-2,4-dione (ADD-3878) and Its Derivatives", Chemical and Pharmaceutical Bulletin, Pharmaceutical Society of Japan, Tokyo, vol. 30, No. 10, Mar. 31, 1982, pp. 3580-3600.

Tanis, Steven P., et al., "Synthesis and Biological Activity of Metabolites of the Antidiabetic, Antihyperglycemic Agent Pioglitazone", Journal of Medicinal Chemistry, American Chemical Society, US, vol. 39, No. 26, 1996, pp. 5053-5063.

\* cited by examiner

SYNTHESIS FOR THIAZOLIDINEDIONE COMPOUNDS

CROSS-REFERENCE TO RELATED APPLICATION

This U.S. patent application claims the benefit of PCT application serial no. PCT/US2011/047010, filed on Aug. 9, 2011, which claims the benefit of U.S. provisional application Ser. no. 61/372,282, filed on Aug. 10, 2010. Each of these documents is hereby incorporated by reference in its entirety.

TECHNICAL FIELD OF THE INVENTION

The present invention provides novel methods for synthesizing PPARγ sparing compounds, e.g., thiazolidinediones, that are useful for preventing and/or treating metabolic disorders such as diabetes, obesity, hypertension, dyslipidemia, and inflammatory diseases.

BACKGROUND OF THE INVENTION

Over the past several decades, scientists have postulated that PPARγ is the generally accepted site of action for insulin sensitizing thiazolidinedione compounds.

Peroxisome Proliferator Activated Receptors (PPARs) are members of the nuclear hormone receptor super-family, which are ligand-activated transcription factors regulating gene expression. PPARs have been implicated in autoimmune diseases and other diseases, i.e., diabetes mellitus, cardiovascular and gastrointestinal disease, and Alzheimer's disease.

PPARγ is a key regulator of adipocyte differentiation and lipid metabolism. PPARγ is also found in other cell types including fibroblasts, myocytes, breast cells, human bone-marrow precursors, and macrophages/monocytes. In addition, PPARγ has been shown in macrophage foam cells in atherosclerotic plaques.

Thiazolidinediones, such as pioglitazone, developed originally for the treatment of type-2 diabetes, generally exhibit high affinity as PPARγ ligands. The finding that thiazolidinediones might mediate their therapeutic effects through direct interactions with PPARγ helped to establish the concept that PPARγ is a key regulator of glucose and lipid homeostasis. However, compounds that involve the activation of PPARγ, such as pioglitazone, also trigger sodium reabsorption and other unpleasant side effects.

SUMMARY OF THE INVENTION

In general, the invention relates to methods of synthesizing compounds that have reduced binding and activation of the nuclear transcription factor PPARγ when compared with high affinity PPARγ ligands such as pioglitazone and rosiglitazone. These novel methods are scalable for industrial production and employ safer, more stable, and/or less costly starting materials and process conditions.

Compounds exhibiting PPARγ activity induce transcription of genes that favor sodium reabsorption. Advantageously, the compounds produced by the syntheses of this invention have reduced binding or activation of the nuclear transcription factor PPARγ when compared with traditional high affinity PPARγ ligands (e.g., pioglitazone or rosiglitazone), and therefore produce fewer or diminished side effects (e.g., reduced augmentation of sodium reabsorption) that are associated with traditional high affinity PPARγ ligands, and are therefore more useful in treating hypertension, diabetes, dyslipidemia, and inflammatory diseases. Most specifically, the reduced PPARγ binding and reduced activity exhibited by these compounds, as compared with traditional high affinity PPARγ ligands (e.g., pioglitazone and rosiglitazone), are particularly useful for treating hypertension, diabetes, dyslipidemia, and inflammatory diseases both as single agents and in combination with other classes of antihypertensive agents. As hypertension and inflammatory diseases pose major risk factors in the onset of diabetes and pre-diabetes, these compounds are also useful for the treatment and prevention of diabetes and other inflammatory diseases. In fact, compounds synthesized by the present invention may induce remission of the symptoms of diabetes in a human patient.

One aspect of the present invention provides a method for preparing a compound of Formula I:

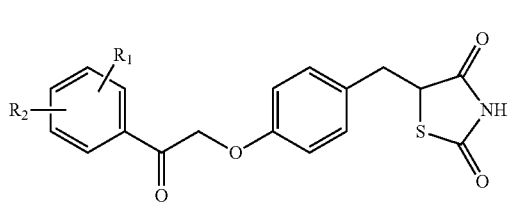

or a pharmaceutically acceptable salt thereof, wherein each of $R_1$ and $R_2$ is independently selected from H, halo, aliphatic, and alkoxy, wherein the aliphatic or alkoxy is optionally substituted with 1-3 of halo; comprising the step of reducing a compound of Formula 2A:

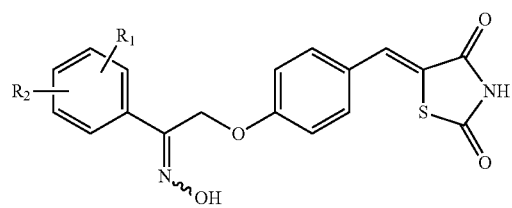

to form a compound of Formula 3A; and

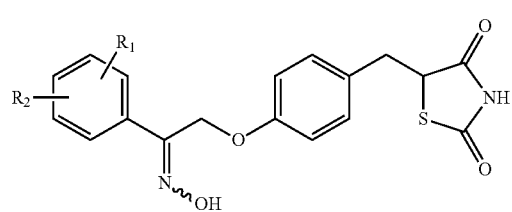

converting the compound of Formula 3A to a compound of Formula I.

Some implementations further comprise converting a compound of Formula 4A

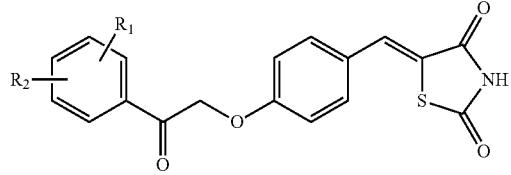

4A into a compound of Formula 2A.

Other implementations further comprise treating the compound of Formula 4A with a reagent comprising HONH$_2$.HCl, HONH$_2$, TMSNHOTMS, (H$_2$NOH)$_2$.H$_2$SO$_4$, or any combination thereof to generate the compound of Formula 2A.

Some implementations further comprising reacting a compound of Formula 5A

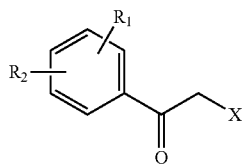

5A wherein X is a leaving group, with the compound of Formula 6A

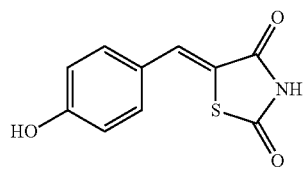

6A to form a compound of Formula 4A.

In some methods, X is a leaving group selected from —Br, —Cl, —I, —OMs, —OTs, —OTf, —OBs, —ONs, —O-tresylate, or —OPO(OR$_4$)$_2$, wherein each R$_4$ is independently C$_{1-4}$ alkyl or two of R$_4$ together with the oxygen and phosphorous atoms to which they are attached form a 5-7 membered ring.

In other methods, the compound of Formula 5A comprises

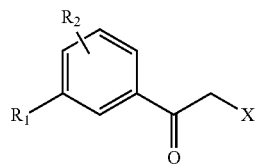

5A1 wherein R$_1$ is selected from a C$_{1-6}$ alkyl or C$_{1-6}$ alkoxy, either of which is optionally substituted with 1-3 halo, and R$_2$ is —H or halo. In some methods, the compound of Formula 5A comprises

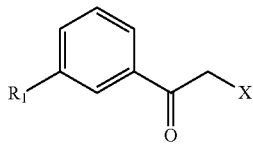

5A2 wherein R$_1$ is selected from a C$_{1-6}$ alkyl or C$_{1-6}$ alkoxy, either of which is optionally substituted with 1-3 halo. In other methods, the compound of Formula 5A comprises

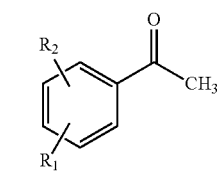

5A3

Some implementations further comprise halogenating a compound of Formula 7A

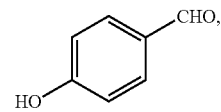

7A to form a compound of Formula 5A.

In some methods, R$_1$ is selected from a C$_{1-6}$ alkyl or C$_{1-6}$ alkoxy, either of which is optionally substituted with 1-3 halo, and R$_2$ is —H or halo. For example, R$_1$ is C$_{1-6}$ alkoxy optionally substituted with 1-3 halo, and R$_2$ is —H. In other examples, R$_1$ is selected from methoxy, ethoxy, or propoxy, any of which is optionally substituted with 1-3 halo.

In other methods, X is selected from —Br and —Cl.

Some implementations further comprise reacting the compound 4-hydroxybenzaldehyde,

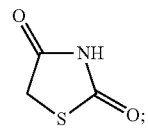

with the compound thiazolidine-2,4-dione, under condensation conditions to form a compound of Formula 6A.

Some implementations further comprise treating the compound of Formula 2A with a reagent comprising NaBH$_4$, LiBH$_4$, KBH$_4$, or any combination thereof and a catalyst comprising CoCl$_2$ to form the compound of Formula 3A.

And, some implementations further comprise treating the compound of Formula 3A with an aqueous acid to form the compound of Formula I. In some methods, the aqueous acid comprises aqueous HCl or aqueous $H_2SO_4$.

Some implementations further comprising reacting a compound of Formula 5B

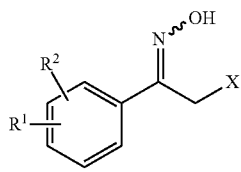

5B wherein X is a leaving group, with a compound of Formula 6A, 5-(4-hydroxybenzylidene)thiazolidine-2,4-dione,

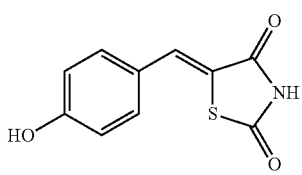

6A to form a compound of Formula 2A.

Some implementations further comprise converting a compound of Formula 5A

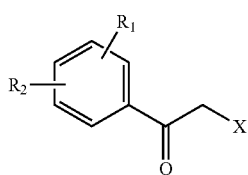

5A to form a compound of Formula 5B.

In some methods, the compound of Formula 5A comprises

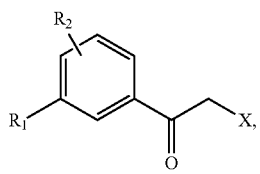

5A1 wherein $R_1$ is selected from a $C_{1-6}$ alkyl or $C_{1-6}$ alkoxy, either of which is optionally substituted with 1-3 halo, and $R_2$ is —H or halo.

In some methods, the compound of Formula 5A comprises

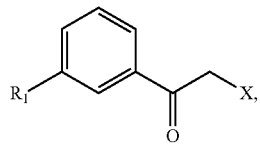

5A2 wherein $R_1$ is selected from a $C_{1-6}$ alkyl or $C_{1-6}$ alkoxy, either of which is optionally substituted with 1-3 halo.

In other methods, the compound of Formula 5A comprises

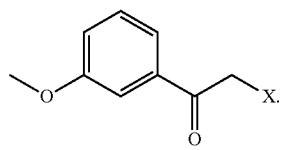

5A3

Some implementations further comprise halogenating a compound of Formula 7A

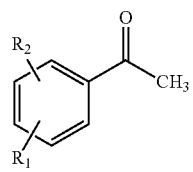

7A to form a compound of Formula 5A.

In some methods, $R_1$ is selected from a $C_{1-6}$ alkyl or $C_{1-6}$ alkoxy, either of which is optionally substituted with 1-3 halo, and $R_2$ is —H or halo. For example, $R_1$ is $C_{1-6}$ alkoxy optionally substituted with 1-3 halo, and $R_2$ is —H. In other methods, $R_1$ is selected from methoxy, ethoxy, or propoxy, any of which is optionally substituted with 1-3 halo.

In other methods, X is selected from —Br and —Cl.

Some implementations further comprising reacting the compound

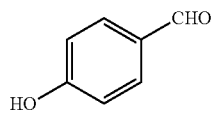

with the compound

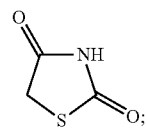

under condensation conditions to form a compound of Formula 6A.

Some implementations further comprise treating the compound of Formula 2A with a reagent comprising $NaBH_4$, LiBH$_4$, KBH$_4$, or any combination thereof and a catalyst comprising CoCl$_2$ to form the compound of Formula 3A.

Some implementations further comprise treating the compound of Formula 3A with an aqueous acid to form a compound of Formula I. In some methods, the aqueous acid comprises aqueous HCl or aqueous H$_2$SO$_4$.

Some implementations further comprise reacting a compound of Formula 8A

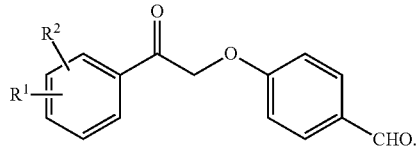

8A with the compound

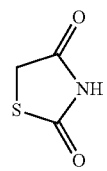

under condensation conditions to form a compound of Formula 4A.

Some implementations further comprising reacting a compound of Formula 5A

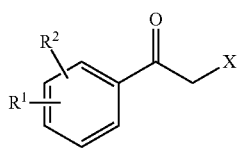

5A with 4-hydroxybenzaldehyde to form a compound of Formula 8A.

In some methods, the compound of Formula 5A comprises

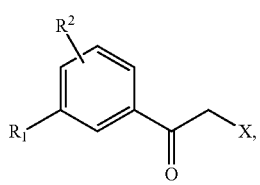

5A1 wherein R$_1$ is selected from a C$_{1-6}$ alkyl or C$_{1-6}$ alkoxy, either of which is optionally substituted with 1-3 halo, and R$_2$ is —H or halo.

In some methods, the compound of Formula 5A comprises

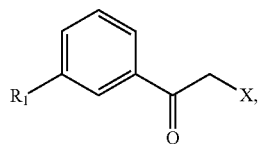

5A2 wherein R$_1$ is selected from a C$_{1-6}$ alkyl or C$_{1-6}$ alkoxy, either of which is optionally substituted with 1-3 halo.

In other methods, the compound of Formula 5A comprises

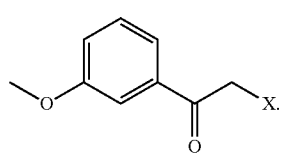

5A3

Some implementations further comprise halogenating a compound of Formula 7A

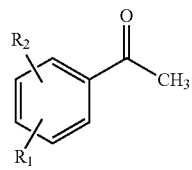

7A to form a compound of Formula 5A.

In some methods, R$_1$ is selected from a C$_{1-6}$ alkyl or C$_{1-6}$ alkoxy, either of which is optionally substituted with 1-3 halo, and R$_2$ is —H or halo. In other methods, R$_1$ is C$_{1-6}$ alkoxy optionally substituted with 1-3 halo, and R$_2$ is —H. And, in some methods, R$_1$ is selected from methoxy, ethoxy, or propoxy, any of which is optionally substituted with 1-3 halo.

In some methods, X is selected from —Br and —Cl.

Some implementations further comprising reacting a compound of Formula 8B

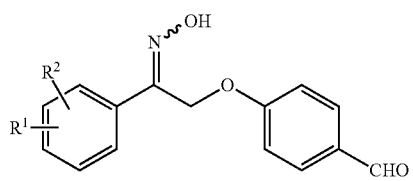

8B with the compound

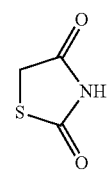

to generate the compound of Formula 2A.

Some implementations further comprise reacting a compound of Formula 5B

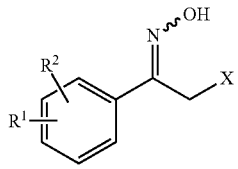

with 4-hydroxybenzaldehyde to form a compound of Formula 8B.

In some methods, the compound of Formula 5B comprises

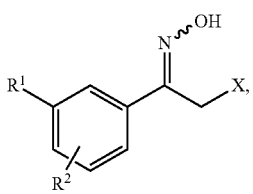

wherein $R_1$ is selected from a $C_{1-6}$ alkyl or $C_{1-6}$ alkoxy, either of which is optionally substituted with 1-3 halo, and $R_2$ is —H or halo.

In other methods, the compound of Formula 5B comprises

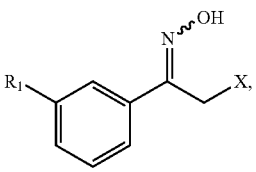

wherein $R_1$ is selected from a $C_{1-6}$ alkyl or $C_{1-6}$ alkoxy, either of which is optionally substituted with 1-3 halo.

In some methods, the compound of Formula 5B comprises

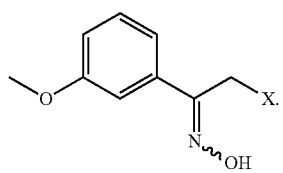

Some implementations further comprise halogenating a compound of Formula 7B

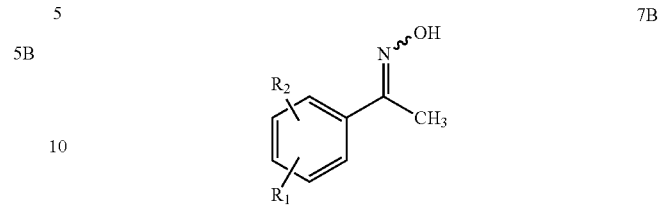

to form a compound of Formula 5B.

In some methods, $R_1$ is selected from a $C_{1-6}$ alkyl or $C_{1-6}$ alkoxy, either of which is optionally substituted with 1-3 halo, and $R_2$ is —H or halo. For example, $R_1$ is $C_{1-6}$ alkoxy optionally substituted with 1-3 halo, and $R_2$ is —H. Or, $R_1$ is selected from methoxy, ethoxy, or propoxy, any of which is optionally substituted with 1-3 halo.

In other methods, X is selected from —Br and —Cl.

Another aspect of the present invention provides a compound of Formula 10A, 10B, or 10C

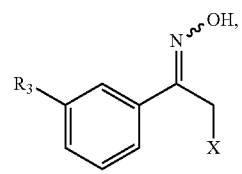

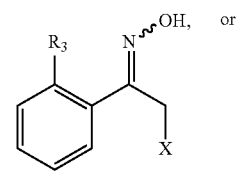

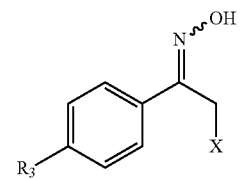

wherein $R_3$ is halo, $C_{1-6}$ alkyl optionally substituted with 1-3 halo, or $C_{1-6}$ alkoxy optionally substituted with 1-3 halo; and X is a leaving group.

Another aspect of the present invention provides a compound Formula 11A, 11B, 11C, 11D, 11E, 11F, 11G, 11H, or 11I

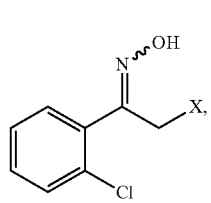

-continued

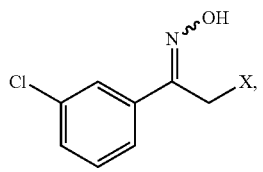  11B

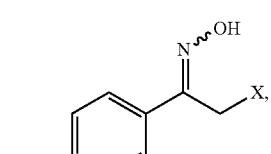  11C

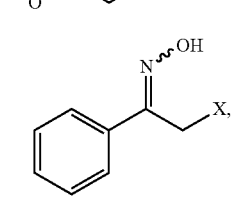  11D

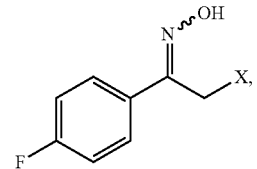  11E

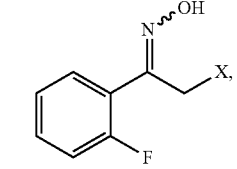  11F

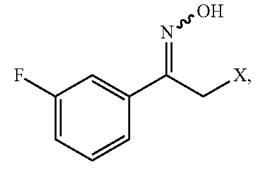  11G

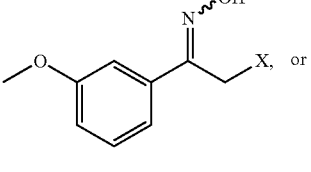  11H

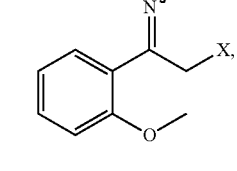  11I wherein X is a leaving group.

In some of the compounds above, X is a leaving group selected from —Br, —Cl, —I, —OMs, —OTs, —OTf, —OBs, —ONs, —O-tresylate, or —OPO(OR$_4$)$_2$, wherein each R$_4$ is independently C$_{1-4}$ alkyl or two of R$_4$ together with the oxygen and phosphorous atoms to which they are attached form a 5-7 membered ring.

Another aspect of the present invention provides a compound of Formula 2A

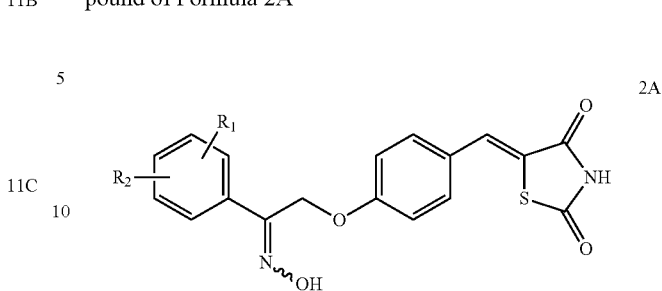

wherein each of R$_1$ and R$_2$ is independently selected from H, halo, aliphatic, and alkoxy, wherein the aliphatic or alkoxy is optionally substituted with 1-3 of halo.

Another aspect of the present invention provides a compound selected from

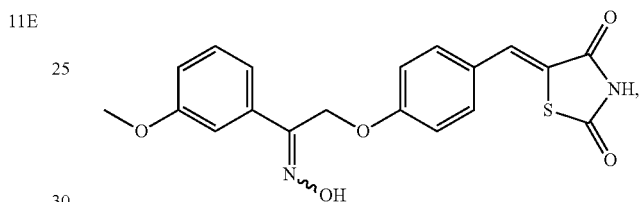

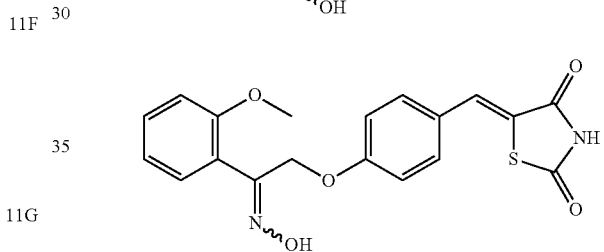

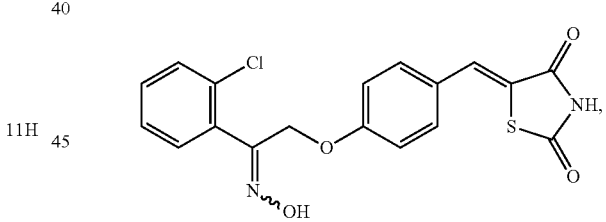

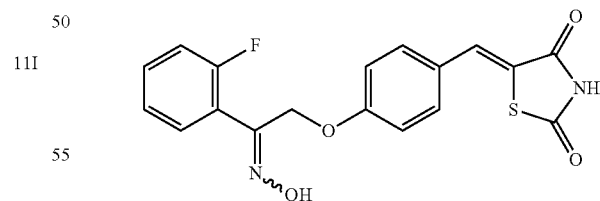

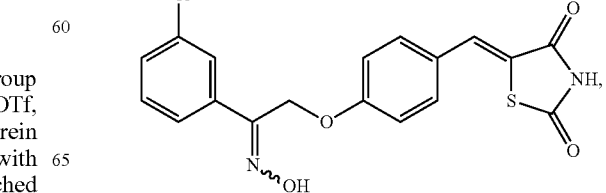

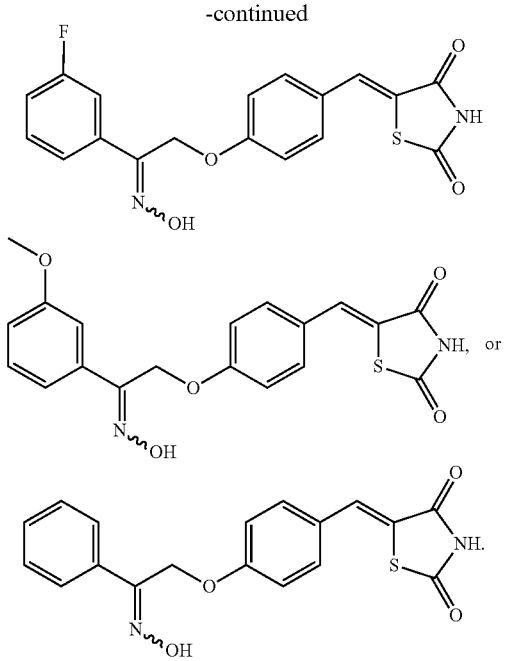

DETAILED DESCRIPTION

The present invention provides novel methods for preparing thiazolidinedione compounds having reduced PPARγ activity.

As used herein, the following definitions shall apply unless otherwise indicated.

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, "protecting group" refers to a moiety or functionality that is introduced into a molecule by chemical modification of a functional group in order to obtain chemoselectivity in a subsequent chemical reaction. Standard protecting groups are provided in Greene and Wuts: "Greene's Protective Groups in Organic Synthesis" 4th Ed, Wuts, P. G. M. and Greene, T. W., Wiley-Interscience, New York: 2006.

As described herein, compounds of the invention may optionally be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ can be aliphatic, cycloaliphatic, aryl, aralphatic, heterocycloaliphatic, heteroaryl or heteroaralphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, aralphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (aralphatic)carbonyl, (heterocycloaliphatic)carbonyl, ((heterocycloaliphatic)aliphatic)carbonyl, (heteroaryl)carbonyl, or (heteroaralphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—, where $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (aralphatic)oxy; (heteroaralphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (aralphatic)carbonyl; (heterocycloaliphatic)carbonyl; ((heterocycloaliphatic)aliphatic)carbonyl; or (heteroaralphatic) carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "aralphatic" such as an "aralkyl" group refers to an aliphatic group (e.g., a $C_{1-4}$ alkyl group) that is substituted with an aryl group. "Aliphatic," "alkyl," and "aryl" are defined herein. An example of an aralphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfonyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)heteroaryl; (hydroxy)heteroaryl; ((carboxy)alkyl)heteroaryl; (((dialkyl)amino)alkyl]heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl; or (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.3.2]decyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure $(R^X)_2N$-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^XO(O)C$-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[$CH_2$]$_v$—, where v is 1-12. A branched aliphatic chain is a straight aliphatic chain that is substituted with one or more aliphatic groups. A branched aliphatic chain has the structure —[CQQ]$_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, $R'_2$, $R_3$, $R_4$, and other variables contained in Formula described herein encompass specific groups, such as alkyl and aryl. Unless otherwise noted, each of the specific groups for the variables $R_1$, $R_2$, $R'_2$, $R_3$, $R_4$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays, or as therapeutic agents.

Chemical structures and nomenclature are derived from ChemDraw, version 11.0.1, Cambridge, Mass.

II. Commonly Used Abbreviations

The following abbreviations are used:
PG protecting group
LG leaving group
DCM dichloromethane
Ac acetyl
DMF dimethylformamide
EtOAc ethyl acetate
DMSO dimethyl sulfoxide
MeCN acetonitrile
TCA trichloroacetic acid
ATP adenosine triphosphate
EtOH ethanol
Ph phenyl
Me methyl
Et ethyl
Bu butyl
DEAD diethylazodicarboxylate
HEPES 4-(2-hydroxyethyl)-1-piperazineethanesulfonic acid
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time
HOBt hydroxybenzotriazole
Ms mesyl
Ts tosyl
Tf triflyl
Bs besyl
Ns nosyl
Cbz carboxybenzyl
Moz p-methoxybenzyl carbonyl
Boc Cert-butyloxycarbonyl
Fmoc 9-fluorenylmethyloxycarbonyl
Bz benzoyl
Bn benzyl
PMB p-methoxybenzyl
DMPM 3,4-dimethoxybenzyl
PMP p-methoxyphenyl

III. Methods of Synthesizing Compounds of Formula I

One aspect of the present invention provides One aspect of the present invention provides a method for preparing a compound of Formula I:

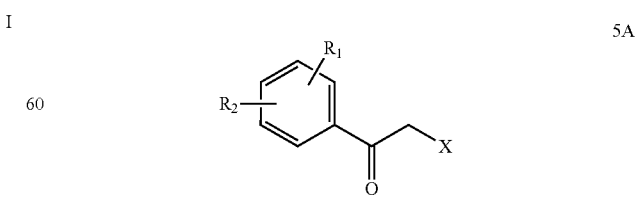

or a pharmaceutically acceptable salt thereof, wherein each of $R_1$ and $R_2$ is independently selected from H, halo, aliphatic, and alkoxy, wherein the aliphatic or alkoxy is optionally substituted with 1-3 of halo; comprising the step of reducing a compound of Formula 2A:

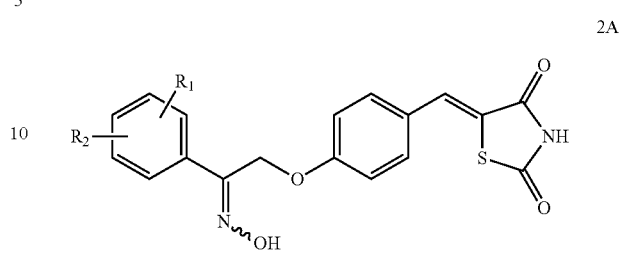

to form a compound of Formula 3A; and

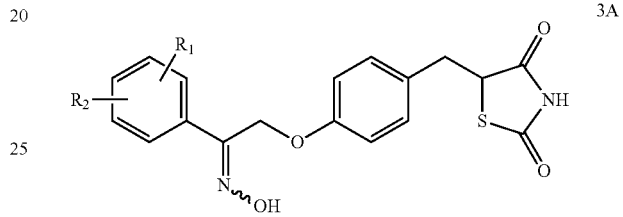

converting the compound of Formula 3A to a compound of Formula I.

Some implementations further comprise converting a compound of Formula 4A

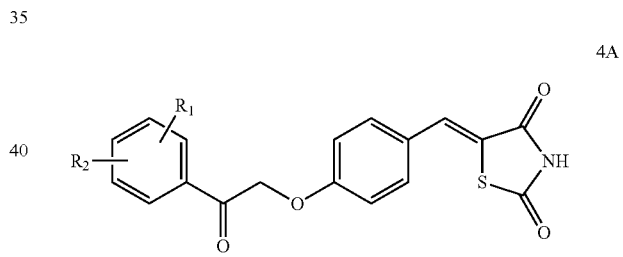

into a compound of Formula 2A.

Other implementations further comprise treating the compound of Formula 4A with a reagent comprising $HONH_2 \cdot HCl$, $HONH_2$, TMSNHOTMS, $(H_2NOH)_2 \cdot H_2SO_4$, or any combination thereof to generate the compound of Formula 2A.

Some implementations further comprising reacting a compound of Formula 5A

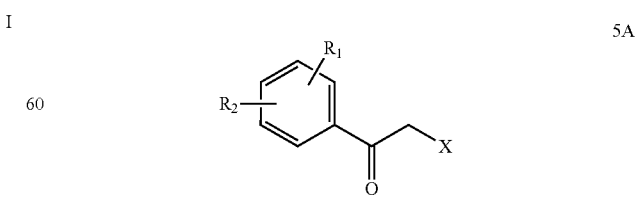

wherein X is a leaving group, with the compound of Formula 6A

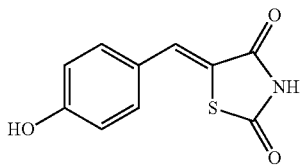

to form a compound of Formula 4A.

In some methods, X is a leaving group selected from —Br, —Cl, —I, —OMs, —OTs, —OTf, —OBs, —ONs, —O-tresylate, or —OPO(OR$_4$)$_2$, wherein each R$_4$ is independently C$_{1-4}$ alkyl or two of R$_4$ together with the oxygen and phosphorous atoms to which they are attached form a 5-7 membered ring.

In other methods, the compound of Formula 5A comprises

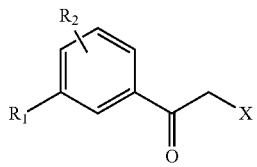

5A1 wherein R$_1$ is selected from a C$_{1-6}$ alkyl or C$_{1-6}$ alkoxy, either of which is optionally substituted with 1-3 halo, and R$_2$ is —H or halo. In some methods, the compound of Formula 5A comprises

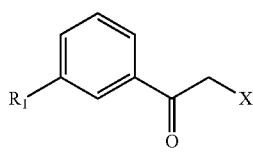

5A2 wherein R$_1$ is selected from a C$_{1-6}$ alkyl or C$_{1-6}$ alkoxy, either of which is optionally substituted with 1-3 halo. In other methods, the compound of Formula 5A comprises

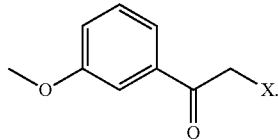

5A3

Some implementations further comprise halogenating a compound of Formula 7A

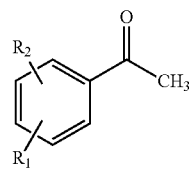

7A to form a compound of Formula 5A.

In some methods, R$_1$ is selected from a C$_{1-6}$ alkyl or C$_{1-6}$ alkoxy, either of which is optionally substituted with 1-3 halo, and R$_2$ is —H or halo. For example, R$_1$ is C$_{1-6}$ alkoxy optionally substituted with 1-3 halo, and R$_2$ is —H. In other examples, R$_1$ is selected from methoxy, ethoxy, or propoxy, any of which is optionally substituted with 1-3 halo.

In other methods, X is selected from —Br and —Cl.

Some implementations further comprise reacting the compound 4-hydroxybenzaldehyde,

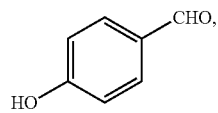

with the compound thiazolidine-2,4-dione,

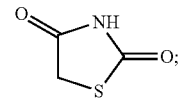

under condensation conditions to form a compound of Formula 6A.

Some implementations further comprise treating the compound of Formula 2A with a reagent comprising NaBH$_4$, LiBH$_4$, KBH$_4$, or any combination thereof and a catalyst comprising CoCl$_2$ to form the compound of Formula 3A.

And, some implementations further comprise treating the compound of Formula 3A with an aqueous acid to form the compound of Formula I. In some methods, the aqueous acid comprises aqueous HCl or aqueous H$_2$SO$_4$.

Some implementations further comprising reacting a compound of Formula 5B

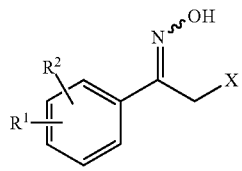

5B wherein X is a leaving group, with a compound of Formula 6A, 5-(4-hydroxybenzylidene)thiazolidine-2,4-dione,

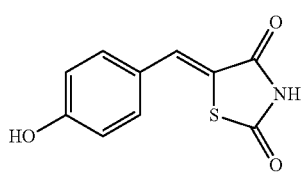

6A to form a compound of Formula 2A.

Some implementations further comprise converting a compound of Formula 5A

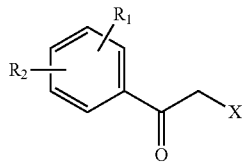

5A to form a compound of Formula 5B.

In some methods, the compound of Formula 5A comprises

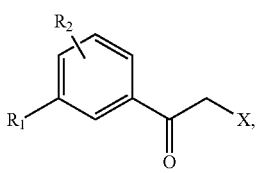

5A1 wherein $R_1$ is selected from a $C_{1-6}$ alkyl or $C_{1-6}$ alkoxy, either of which is optionally substituted with 1-3 halo, and $R_2$ is —H or halo.

In some methods, the compound of Formula 5A comprises

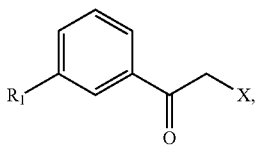

5A2 wherein $R_1$ is selected from a $C_{1-6}$ alkyl or $C_{1-6}$ alkoxy, either of which is optionally substituted with 1-3 halo.

In other methods, the compound of Formula 5A comprises

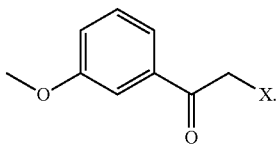

5A3

Some implementations further comprise halogenating a compound of Formula 7A

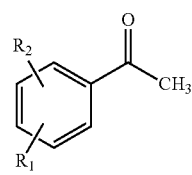

7A to form a compound of Formula 5A.

In some methods, $R_1$ is selected from a $C_{1-6}$ alkyl or $C_{1-6}$ alkoxy, either of which is optionally substituted with 1-3 halo, and $R_2$ is —H or halo. For example, $R_1$ is $C_{1-6}$ alkoxy optionally substituted with 1-3 halo, and $R_2$ is —H. In other methods, $R_1$ is selected from methoxy, ethoxy, or propoxy, any of which is optionally substituted with 1-3 halo.

In other methods, X is selected from —Br and —Cl.

Some implementations further comprising reacting the compound

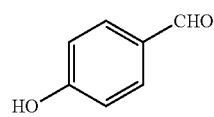

with the compound

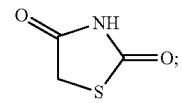

under condensation conditions to form a compound of Formula 6A.

Some implementations further comprise treating the compound of Formula 2A with a reagent comprising $NaBH_4$, $LiBH_4$, $KBH_4$, or any combination thereof and a catalyst comprising $CoCl_2$ to form the compound of Formula 3A.

Some implementations further comprise treating the compound of Formula 3A with an aqueous acid to form a compound of Formula I. In some methods, the aqueous acid comprises aqueous HCl or aqueous $H_2SO_4$.

Some implementations further comprise reacting a compound of Formula 8A

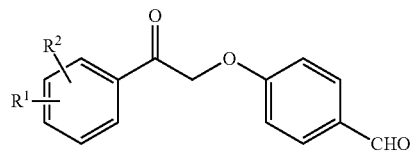

8A with the compound

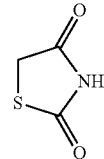

under condensation conditions to form a compound of Formula 4A.

Some implementations further comprising reacting a compound of Formula 5A

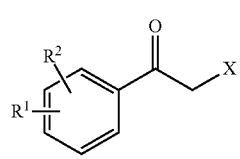

5A with 4-hydroxybenzaldehyde to form a compound of Formula 8A.

In some methods, the compound of Formula 5A comprises

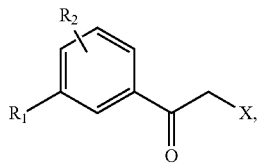

5A1 wherein $R_1$ is selected from a $C_{1-6}$ alkyl or $C_{1-6}$ alkoxy, either of which is optionally substituted with 1-3 halo, and $R_2$ is —H or halo.

In some methods, the compound of Formula 5A comprises

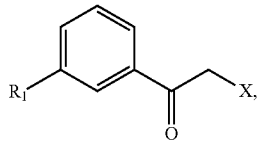

5A2 wherein $R_1$ is selected from a $C_{1-6}$ alkyl or $C_{1-6}$ alkoxy, either of which is optionally substituted with 1-3 halo.

In other methods, the compound of Formula 5A comprises

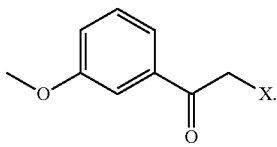

5A3

Some implementations further comprise halogenating a compound of Formula 7A

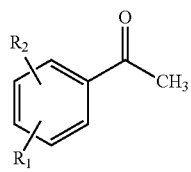

7A to form a compound of Formula 5A.

In some methods, $R_1$ is selected from a $C_{1-6}$ alkyl or $C_{1-6}$ alkoxy, either of which is optionally substituted with 1-3 halo, and $R_2$ is —H or halo. In other methods, $R_1$ is $C_{1-6}$ alkoxy optionally substituted with 1-3 halo, and $R_2$ is —H. And, in some methods, $R_1$ is selected from methoxy, ethoxy, or propoxy, any of which is optionally substituted with 1-3 halo.

In some methods, X is selected from —Br and —Cl.

Some implementations further comprising reacting a compound of Formula 8B

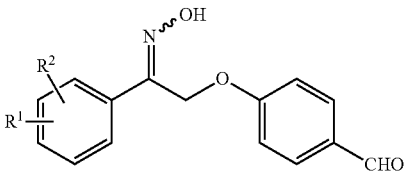

8B with the compound

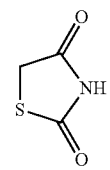

to generate the compound of Formula 2A.

Some implementations further comprise reacting a compound of Formula 5B

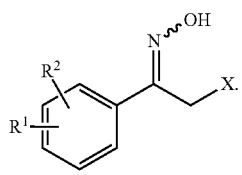

5B with 4-hydroxybenzaldehyde to form a compound of Formula 8B.

In some methods, the compound of Formula 5B comprises

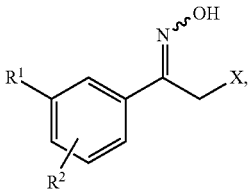

5B1 wherein $R_1$ is selected from a $C_{1-6}$ alkyl or $C_{1-6}$ alkoxy, either of which is optionally substituted with 1-3 halo, and $R_2$ is —H or halo.

In other methods, the compound of Formula 5B comprises

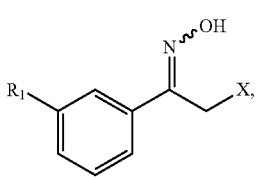

5B2 wherein $R_1$ is selected from a $C_{1-6}$ alkyl or $C_{1-6}$ alkoxy, either of which is optionally substituted with 1-3 halo.

In some methods, the compound of Formula 5B comprises

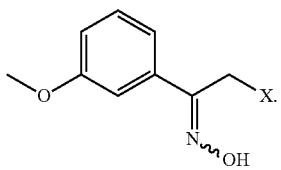

5B3

Some implementations further comprise halogenating a compound of Formula 7B

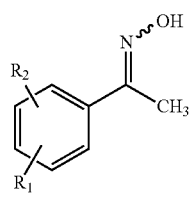

7B to form a compound of Formula 5B.

In some methods, $R_1$ is selected from a $C_{1-6}$ alkyl or $C_{1-6}$ alkoxy, either of which is optionally substituted with 1-3 halo, and $R_2$ is —H or halo. For example, $R_1$ is $C_{1-6}$ alkoxy optionally substituted with 1-3 halo, and $R_2$ is —H. Or, $R_1$ is selected from methoxy, ethoxy, or propoxy, any of which is optionally substituted with 1-3 halo.

In other methods, X is selected from —Br and —Cl.

IV. Exemplary Syntheses

The following synthetic schemes represent example embodiments of the present invention:

Scheme 1:

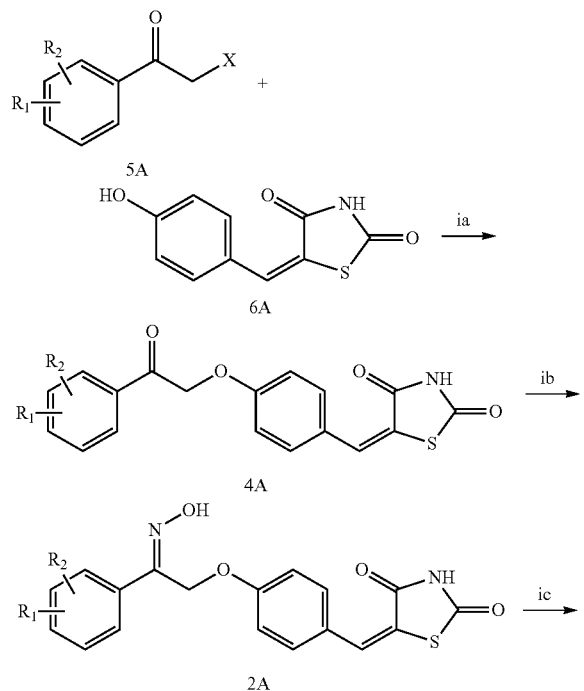

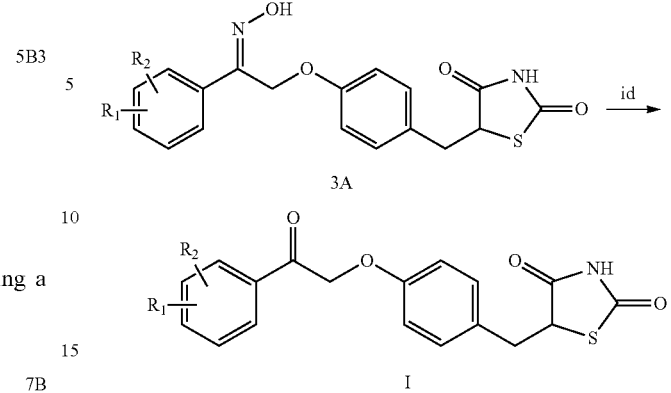

wherein $R^1$, $R^2$ and X are defined above.

In step ia, starting materials 5A and 6A are reacted under alkylation conditions (e.g., KO'Bu in DMSO) to generate intermediate 4A. Intermediate 4A is converted to the corresponding oxime intermediate 2A in step ib. Intermediate 2A is reduced to generate intermediate 3A in step ic, and intermediate 3A is converted to a compound of Formula I in step id.

In some embodiments, starting material 5A is generated according to Scheme 1A.

Scheme 1A:

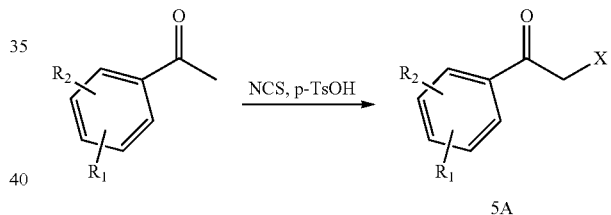

wherein X is —Cl.

In Scheme 1A, the acetophenone undergoes halogenation to generate starting material 5A.

In several embodiments, the starting material 6A is generated according to Scheme 1B, below:

Scheme 1B:

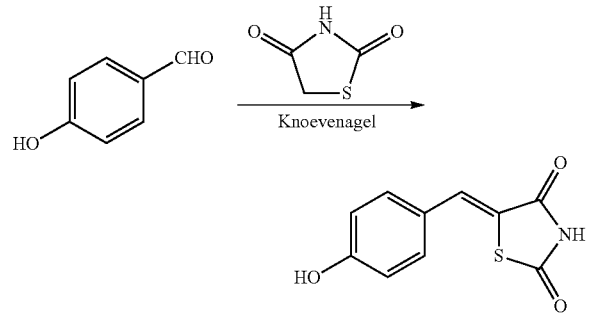

In some embodiments, the compound of Formula I is generated according to Scheme 2.

Scheme 2:

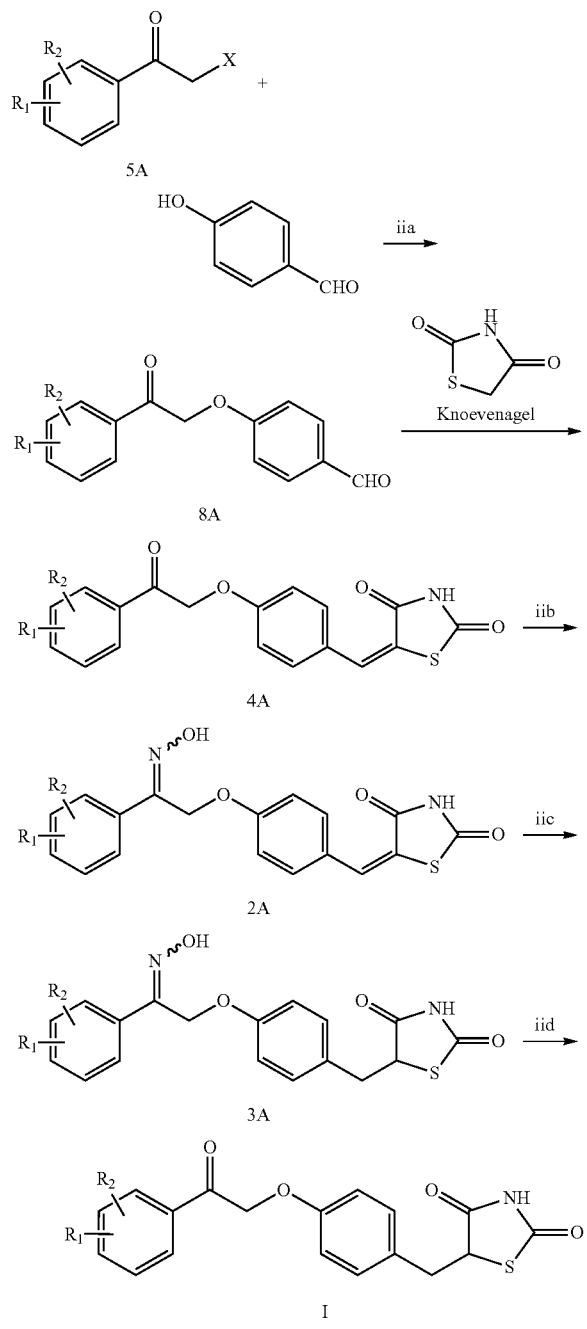

wherein $R^1$, $R^2$ and X are defined above.

In step iia, starting material 5A and 4-hydroxybenzaldehyde are reacted under alkylation conditions (e.g., KO$^t$Bu in DMSO) to generate intermediate 8A. Intermediate 8A is converted to intermediate 4A, and, in step iib, intermediate 4A is converted to the corresponding oxime intermediate 2A. In step iic, oxime intermediate 2A undergoes reduction to generate the intermediate 3A, which is then converted to a compound of Formula I in step iid.

In some embodiments, the compound of Formula I is generated according to Scheme 3.

Scheme 3:

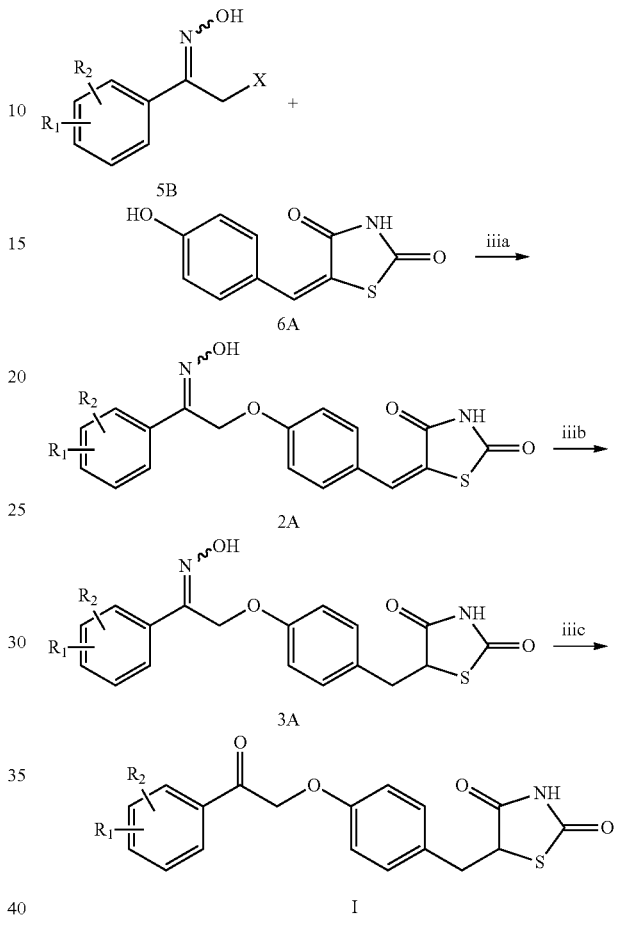

wherein $R_1$, $R_2$, and X are defined above.

In step iiia, starting materials 5A and 6A are reacted under alkylation conditions (e.g., KO$^t$Bu in DMSO) to generate intermediate 2A, which undergoes reduction in step iiib to generate intermediate 3A. Intermediate 3A is then converted to a compound of Formula I in step iiic.

In some embodiments, starting material 5B is generated according to Scheme 3A.

Scheme 3A:

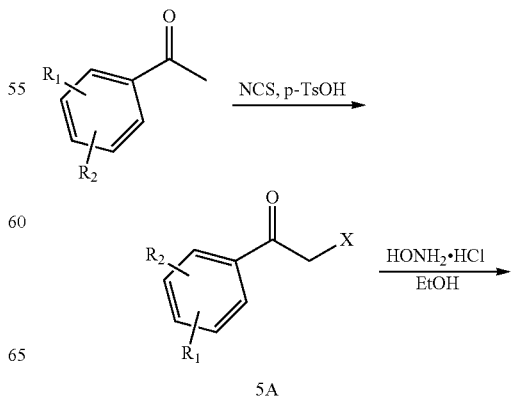

-continued

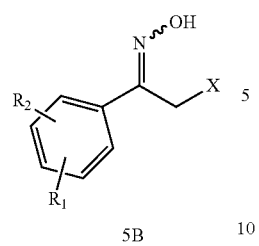

5B wherein X is —Cl.

In some embodiments, the compound of Formula I is generated according to Scheme 4.

Scheme 4:

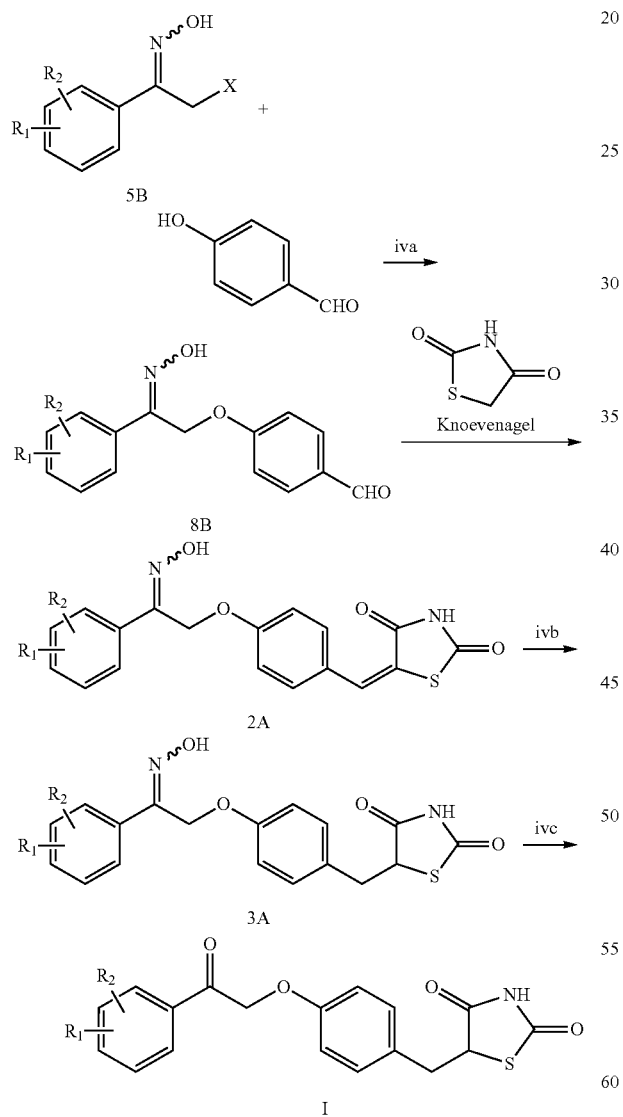

In step iva, starting material 5B and 4-hydroxybenzaldehyde are reacted under alkylation conditions (e.g., KO'Bu in DMSO) to generate intermediate 8B. Intermediate 8B is converted to intermediate 2A, and, in step ivb, intermediate 2A is undergoes reduction to generate the intermediate 3A, which is then converted to a compound of Formula I in step ivc.

V. Novel Compounds

Another aspect of the present invention provides a compound of Formula 10A, 10B, or 10C

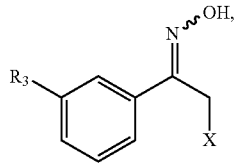

10A

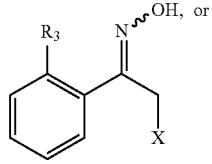

10B

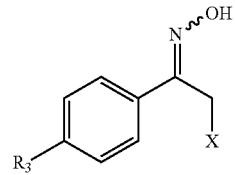

10C wherein $R_3$ is halo, $C_{1-6}$ alkyl optionally substituted with 1-3 halo, or $C_{1-6}$ alkoxy optionally substituted with 1-3 halo; and X is a leaving group, as defined above.

Another aspect of the present invention provides a compound of Formula 11A, 11B, 11C, 11D, 11E, 11F, 11G, 11H, or 11I

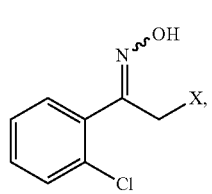

11A

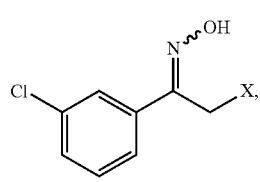

11B

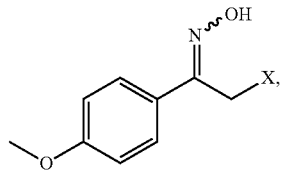

11C

-continued
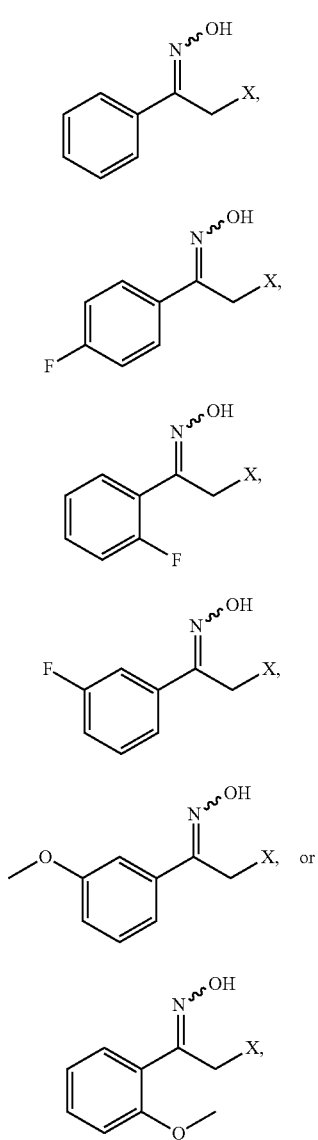
wherein X is a leaving group, as defined above.
And, another aspect of the present invention provides a compound of Formula 2A
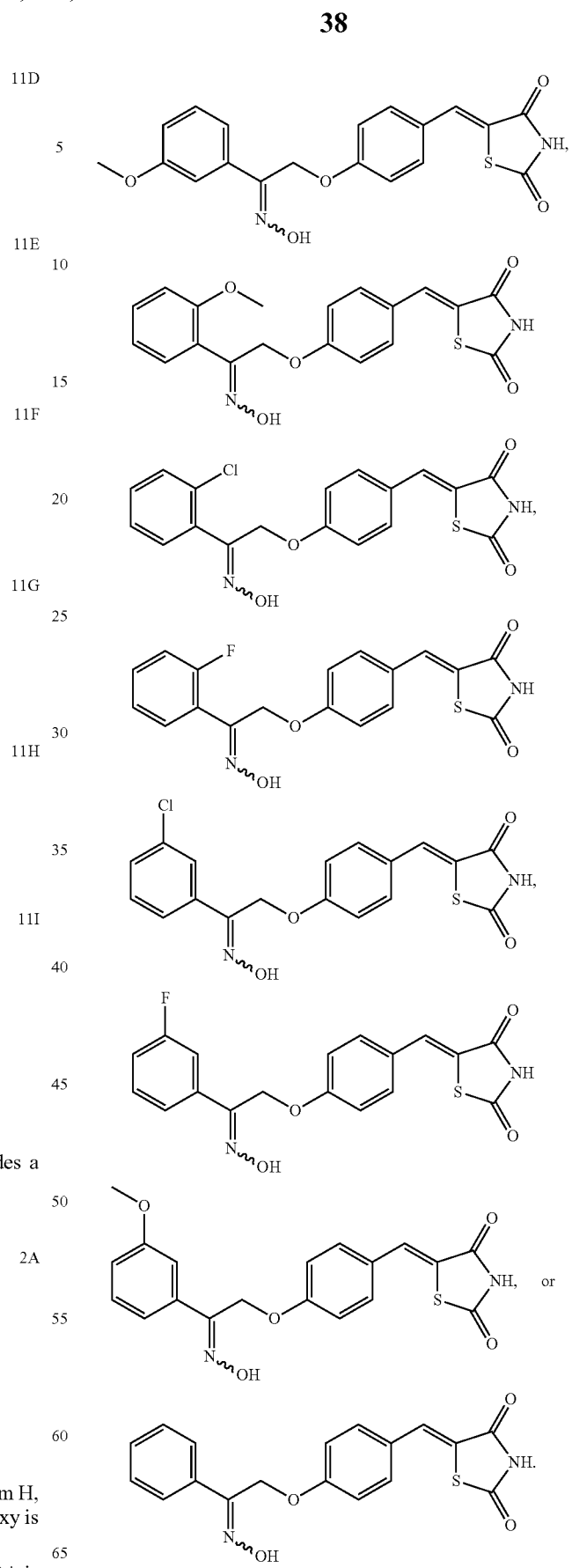
wherein each of $R_1$ and $R_2$ is independently selected from H, halo, aliphatic, and alkoxy, wherein the aliphatic or alkoxy is optionally substituted with 1-3 of halo.
In several embodiments, the compound of Formula 2A is selected from

VI. EXAMPLES

Example 1

Preparation of (Z)-5-(4-(2-(3-methoxyphenyl)-2-oxoethoxy)benzylidene)thiazolidine-2,4-dione

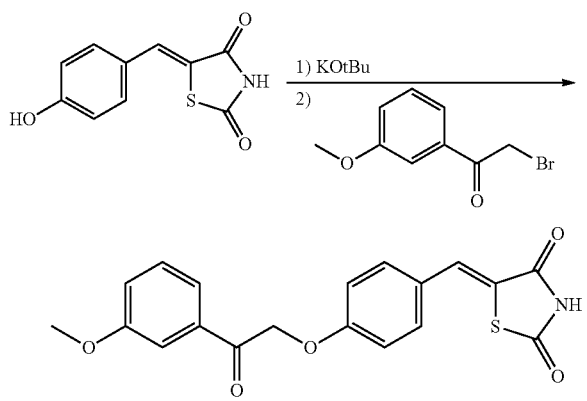

To a stirring solution of 5-(4-hydroxybenzyl)thiazolidine-2,4-dione (100 mg, 0.4 mmol) in DMSO (2 ml), potassium tert-butoxide (106 mg, 0.941 mmol) was added. Stirring continued at RT for about 1 hour. 2-Bromo-3'-methoxyacetophenone (100 mg, 0.5 mmol) was then added to the mixture. After 2 hours, LCMS showed that the reaction was complete. The reaction mixture was partitioned between EtOAc and water, and the aqueous phase was extracted with EtOAc. Combined extracts were washed with brine, dried on ($Na_2SO_4$), filtered, and evaporated in vacuo. The residue was chromatographed on a small RediSep column eluting with 0-10% acetone/DCM. Fractions containing the product were combined and evaporated in vacuo to afford 70 mg of 5-{4-[2-(3-methoxyphenyl)-2-oxoethoxy]benzyl}-1,3-thiazolidine-2,4-dione as a pale yellow solid. $^1$H-NMR (DMSO-d6): δ 12.49 (brs, 1H), 7.72(s, 1H), 7.59(m, 1H), 7.53-7.46(m, 4H), 7.24(dd, J=8.2, 2.4 Hz, 1H), 7.10(d, J=8.7 Hz, 2H), 5.66(s, 2H), (3.80 (s, 3H). HPLC: 3.969 min., 61 area % @2540 nm; 3.969 min., 62 area % @210 nm. MS (ESI−) for $C_{19}H_{15}NO_5S$ m/z 368.4 $(M-H)^-$.

Example 2

Preparation of (5Z)-5-(4-(2-(hydroxyimino)-2-(3-methoxyphenyl)ethoxy)benzylidene)thiazolidine-2,4-dione

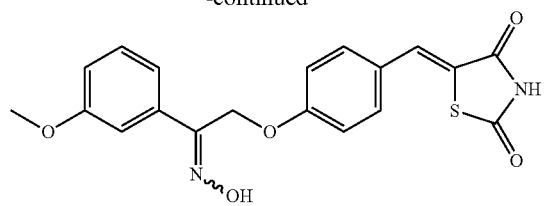

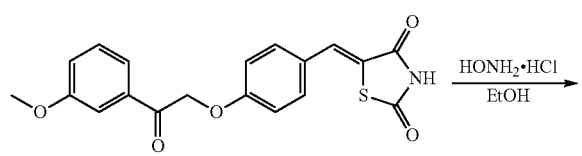

A stirring suspension of (5Z)-5-{4-[2-(3-methoxyphenyl)-2-oxoethoxy]benzylidene}-1,3-thiazolidine-2,4-dione (1.42 g, 3.84 mmol; Supplier=Kalexsyn; Lot=1003-TTP-149) in THF (15 ml) was heated with a heat gun—no solution. Added DMF (5 ml) and heated—no solution. Added another 5 ml DMF and heated until all solids dissolved. The hydroxylamine hydrochloride was added portionwise. Added $HONH_2 \cdot HCl$ (100 mg) and allowed to sit at RT overnight. HPLC showed a ratio of ca. 2:1 SM:pdt. Added 100 mg $HONH_2 \cdot HCl$. After 4 hours there was little change in HPLC. Added 100 mg $HONH_2 \cdot HCl$ and left to stir over the weekend. The reaction was complete. The reaction mixture was partitioned between EtOAc (30 ml) and 1M $KHSO_4$ (30 ml). The aqueous phase was extracted with EtOAc (30 ml). The combined organic phases were washed with saturated $NaHCO_3$ (30 ml), brine (30 ml), dried ($Na_2SO_4$), filtered and evaporated in vacuo to give 1.34 g yellow solid. $^1$H-NMR (DMSO-d6): δ 12.53(brs, 1H), 12.02(brs, 1H), 7.73(s, 1H), 7.54(d, J=8.9 Hz, 2H), 7.30(t, J=7.9 Hz, 1H), 7.20(m, 2H), 7.10(d, J=8.9 Hz, 2H), 6.95(dd, J=8.1, 2.5 Hz, 1H), 5.31(s, 2H), 3.74(s, 3H). HPLC: 3.690 min., 10 area %, and 3.788 min., 89 area % @ 210 nm; 3.690 min., 6 area %, and 3.789 min., 94 area % @ 254 nm. MS (ESI−) for $C_{19}H_{16}N_2O_5S$ m/z 383.3 $(M-H)^-$.

Example 3

Preparation of 5-(4-(2-(hydroxyimino)-2-(3-methoxyphenyl)ethoxy)benzyl)thiazolidine-2,4-dione

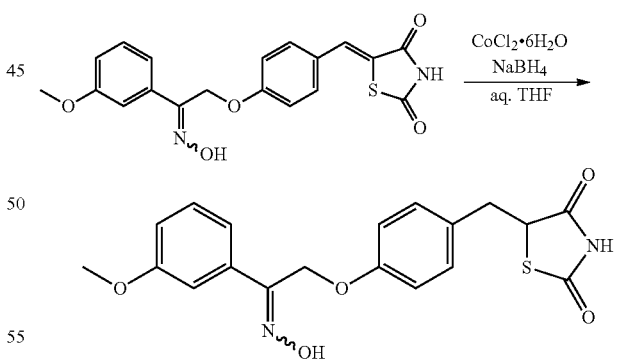

To a stirring suspension of (5Z)-5-(4-{[(2Z)-2-(hydroxyimino)-2-(3-methoxyphenyl)ethyl]oxy}benzylidene)-1,3-thiazolidine-2,4-dione (815 mg, 2.12 mmol) in THF/$H_2O$ (15 ml) was added cobalt chloride hexahydrate (2 mg) and 2,2'-bipyridine (8 mg). Stirred at RT for 10 minutes. Added $NaBH_4$ portionwise until characteristic deep blue color was observed. When the color faded to give a yellow/orange solution, $NaHBH_4$ was added portionwise until deep blue color persisted. Left to stir at RT overnight. The reaction was judged complete by HPLC. Adjusted pH to 6-7 with HOAc, then extracted with EtOAc (2×25 ml). The combined extracts were washed with brine, dried (Na$_2$SO$_4$), filtered and evaporated in vacuo to afford a 780 mg of a light yellow solid which was washed with DCM. $^1$H-NMR (DMSO-d6): δ 11.35(brs, 1H), 11.04(brs, 1H), 7.16 (m, 3H), 7.02(d, J=8.5 Hz, 2H), 6.80(m, 3H), 5.13(s, 2H), 4.33(dd, J=9.6, 3.8 Hz, 1H), 3.69(s, 3H), 3.33(dd, J=141, 9.5 Hz, 1H), 2.94(dd, J=14.1, 9.5 Hz, 1H). HPLC: 3.513 min., 15 area %, and 3.610 min., 77 area % @ 210 nm; 3.513 min., 11 area %, and 3.610 min., 89 area % @ 254 nm. MS (ESI−) for C$_{19}$H$_{18}$N$_2$O$_5$S m/z 387.2 (M+H)$^+$; m/z 385.2 (M−H)$^-$.

Example 4

Preparation of 5-(4-(2-(3-methoxyphenyl)-2-oxoethoxy)benzyl)thiazolidine-2,4-dione

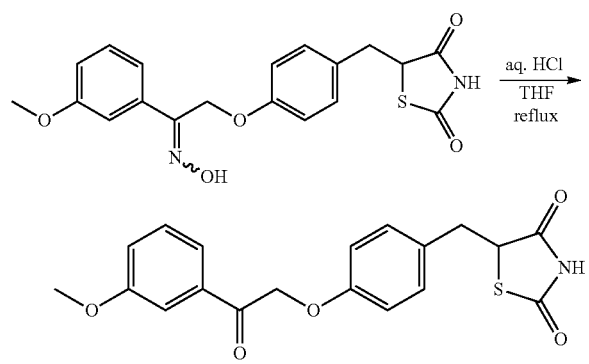

A stirring solution of 5-(4-{[(2Z)-2-(hydroxyimino)-2-(3-methoxyphenyl)ethyl]oxy}benzyl)-1,3-thiazolidine-2,4-dione (0.76 g, 2.0 mmol; Supplier=Kalexsyn; Lot=1003-TTP-124) in THF (5 ml) and 6M HCl (5 ml) was heated to reflux. Little reaction after 4 hours at reflux. Left to reflux overnight. Reaction is complete. 2N NaOH was added until the reaction mixture was ca. pH 8-9. The reaction mixture was extracted with EtOAc (2×25 ml). The combined extracts were washed with brine, dried (Na$_2$SO$_4$), filtered and evaporated in vacuo to give a light yellow oily solid. This material was treated with 5% MeOH/DCM (10 ml) and the resulting white solids were collected by suction filtration and dried to afford 495 mg of final product. $^1$H-NMR (DMSO-d6): δ 12.03(s, 1H), 7.62(d, J=7.7 Hz, 1H), 7.49((m, 2H), 7.27(dd, J=8.2, 2.6 Hz, 1H), 7.15(d, J=8.7 Hz, 2H), 6.91(d, J=8.5 Hz, 2H), 5.55(s, 2H), 4.88(dd, J=9.1, 4.3 Hz, 1H), 3.83(s, 3H), 3.31(m, 1H), 3.31 (m, 1H), 3.05(dd, J=14.1, 9.3 Hz, 1H). HPLC: 3.782 min., 93 area % @ 210 nm; 3.785 min. 100 area % @ 254 nm. MS (ESI−) for C$_{19}$H$_{17}$NO$_5$S m/z 370.1 (M−H)$^-$.

Example 5

Assays

Assays for Measuring Reduced PPARγ Receptor Activation

Whereas activation of the PPARγ receptor is generally believed to be a selection criteria to select for molecules that may have anti-diabetic and insulin sensitizing pharmacology, this invention finds that activation of this receptor should be a negative selection criterion. Molecules will be chosen from this chemical space because they have reduced, not just selective, activation of PPARγ. The optimal compounds have at least a 10-fold reduced potency as compared to pioglitazone and less than 50% of the full activation produced by rosiglitazone in assays conducted in vitro for transactivation of the PPARγ receptor. The assays are conducted by first evaluation of the direct interactions of the molecules with the ligand binding domain of PPARγ. This can be performed with a commercial interaction kit that measures the direct interaction by florescence using rosiglitazone as a positive control. Further assays can be conducted in a manner similar to that described by Lehmann et al. [Lehmann J M, Moore L B, Smith-Oliver T A: An Antidiabetic Thiazolidinedione is a High Affinity Ligand for Peroxisome Proliferator-activated Receptor (PPAR) J. Biol. Chem. (1995) 270: 12953] but will use luciferase as a reporter as in Vosper et al. [Vosper, H., Khoudoli, G A, Palmer, C N (2003) The peroxisome proliferators activated receptor d is required for the differentiation of THP-1 moncytic cells by phorbol ester. Nuclear Receptor 1:9]. Compound stocks will be dissolved in DMSO and added to the cell cultures at final concentrations of 0.1 to 100 μM and the relative activation will be calculated as induction of the reporter gene (luciferase) as corrected for by the expression of the control plasmid (coding for galactosidase). Pioglitazone and rosiglitazone will be used as reference compounds as described above.

In addition to showing the reduced activation of the PPARγ receptor in vitro, the compounds will not produce significant activation of the receptor in animals. Compounds dosed to full effect for insulin sensitizing actions in vivo (see below) will be not increase activation of PPARγ in the liver as measured by the expression of a P2, a biomarker for ectopic adipogenesis in the liver [Matsusue K, Haluzik M, Lambert G, Yim S-H, Oksana Gavrilova O, Ward J M, Brewer B, Reitman M L, Gonzalez F J. (2003) Liver-specific disruption of PPAR in leptin-deficient mice improves fatty liver but aggravates diabetic phenotypes. J. Clin. Invest.; 111: 737] in contrast to pioglitazone and rosiglitazone, which do increase a P2 expression under these conditions.

The insulin sensitizing and antidiabetic pharmacology are measured in the KKAY mice as previously reported [Hofmann, C., Lornez, K., and Colca, J. R. (1991). Glucose transport deficiency corrected by treatment with the oral anti-hyperglycemic agent Pioglitazone. Endocrinology, 129: 1915-1925.] Compounds are formulated in 1% sodium carboxy methylcellulose, and 0.01% tween 20 and dosed daily by oral gavage. After 4 days of once daily treatment, treatment blood samples are taken from the retro-orbital sinus and analyzed for glucose, triglycerides, and insulin as described in Hofmann et al. Doses of compounds that produce at least 80% of the maximum lowering of glucose, triglycerides, and insulin will not significantly increase the expression of a P2 in the liver of these mice.

Measuring PPARγ Receptor Activation

The ability of several exemplary compounds of the present invention to bind to PPARγ was measured using a commercial binding assay (Invitrogen Corporation, Carlsbad, Calif.) that measures the test compounds ability to bind with PPAR-LBD/Fluormone PPAR Green complex. These assays were performed on three occasions with each assay using four separate wells (quadruplicate) at each concentration of tested compound. The data are mean and SEM of the values obtained from the three experiments. Rosiglitazone was used as the positive control in each experiment. Compounds were added at the concentrations shown, which range from 0.1-100 micromolar.

Glucose, Insulin, and Triglyceride in Diabetic KKAy Mice Treated with Exemplary Compounds of the Present Invention.

The insulin sensitizing and antidiabetic pharmacology are measured in the KKAy mice as previously reported [Hofmann, C., Lornez, K., and Colca, J. R. (1991). Glucose transport deficiency corrected by treatment with the oral antihyperglycemic agent Pioglitazone. Endocrinology, 129: 1915-1925.]. Compounds are formulated in 1% sodium carboxy methylcellulose, and 0.01% tween 20 and dosed daily by oral gavage. After 4 days of once daily treatment, blood samples are taken from the retro-orbital sinus and analyzed for glucose, triglycerides, and insulin as described in Hofmann et al. Doses of compounds that produce at least 80% of the maximum lowering of glucose, triglycerides, and insulin will not significantly increase the expression of a P2 in the liver of these mice.

Compounds were formulated by suspension and orally dosed to KKAy mice at 93 mg/kg for 4 days. The compounds were first dissolved in DMSO and then placed into aqueous suspension containing 7-10% DMSO, 1% sodium methylcarboxycellulose, and 0.01% Tween 20. On the fifth day, the mice were fasted and blood samples were obtained approximately 18 hours after the last dose. The parameters were measured by standard assay methods. Data are mean and SEM N=6-12 mice.

TABLE A

Assay Results

| Example Description | Cmpd No. | Glucose (Mean/SD) | Insulin (Mean/SD) | TG (Mean/SD) |
| --- | --- | --- | --- | --- |
| Vehicle A | | 518<br>59 | 24<br>5 | 284<br>36 |
| 5-[4-(2-oxo-2-phenylethoxy)benzyl]-1,3-thiazolidine-2,4-dione | 1 | 0.71<br>0.03 | 0.13<br>0.02 | 0.56<br>0.05 |
| 5-{4-[2-(4-fluorophenyl)-2-oxoethoxy]benzyl}-1,3-thiazolidine-2,4-dione | 2 | 0.61<br>0.02 | 0.10<br>0.02 | 0.45<br>0.02 |
| 5-{4-[2-(2-fluorophenyl)-2-oxoethoxy]benzyl}-1,3-thiazolidine-2,4-dione | 3 | 0.64<br>0.02 | 0.20<br>0.07 | 0.62<br>0.04 |
| 5-{4-[2-(3-fluorophenyl)-2-oxoethoxy]benzyl}-1,3-thiazolidine-2,4-dione | 4 | 0.62<br>0.05 | 0.24<br>0.05 | 0.46<br>0.07 |

TABLE A-continued

Assay Results

| Example Description | Cmpd No. | Glucose (Mean/SD) | Insulin (Mean/SD) | TG (Mean/SD) |
|---|---|---|---|---|
| 5-{4-[2-(3-methoxyphenyl)-2-oxoethoxy]benzyl}-1,3-thiazolidine-2,4-dione | 5 | 0.56 0.05 | 0.22 0.03 | 0.41 0.06 |
| 5-{4-[2-(2-methoxyphenyl)-2-oxoethoxy]benzyl}-1,3-thiazolidine-2,4-dione | 6 | 0.75 0.04 | 1.20 0.27 | 0.80 0.11 |
| 5-{4-[2-(3-chlorophenyl)-2-oxoethoxy]benzyl}-1,3-thiazolidine-2,4-dione | 7 | 0.54 0.03 | 0.59 0.33 | 0.43 0.04 |

Compound Nos. 1-5 exhibited a plasma insulin level of less than about 5 ng/ml and compound no. 6 exhibited a plasma insulin level between about 15 and 20 ng/ml; compound nos. 1, 2, 3, 4, and 5 exhibited a plasma triglyceride level of between about 100 and 200 mg/dl, and compound no. 6 exhibited a plasma triglyceride level between about 300 and 400 mg/dl; compound nos. 1, 2, 3, 4, and 5 exhibited a plasma glucose level of between about 350 and 425 mg/dl and compound no. 6 exhibited a plasma glucose level between about 450 and 525 mg/dl.

The PPARγ-sparing compounds of this invention will be more effective for the treatment of diseases caused by metabolic inflammation such as diabetes and metabolic syndrome by limiting the side effects attributable to direct and partial activation of nuclear transcription factors.

Because the compounds of the present invention exhibit reduced PPARγ activation, it is anticipated that these compounds are suitable for use in combination with other compounds having antidiabetic activity, such as metformin, DDP-4 inhibitors, or other antidiabetic agents that function by differing mechanisms to augment the actions or secretions of GLP1 or insulin. Specifically because of the reduced PPARγ interaction, these compounds will also be useful for treating dyslipidemia associated with metabolic inflammatory diseases combining particularly well with lipid lowering statins such as atorvastatin or the like. It is also anticipated that the combination of a compound of Formula I and other antidiabetic compounds will be more effective in treating diabetes than combinations with PPAR-activating compounds as they will avoid side effects associated with PPARγ activation that may include volume expansion, edema, and bone loss.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for preparing a compound of Formula I:

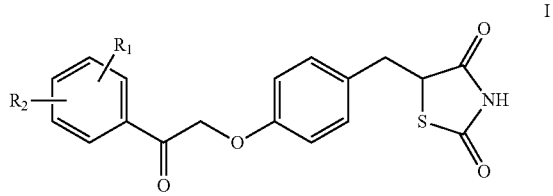

or a pharmaceutically acceptable salt thereof, wherein

Each of $R_1$ and $R_2$ is independently selected from H, halo, aliphatic, and alkoxy, wherein the aliphatic or alkoxy is optionally substituted with 1-3 of halo;

comprising the step of:

reducing a compound of Formula 2A:

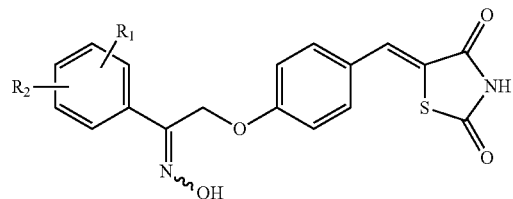

2A to form a compound of Formula 3A; and

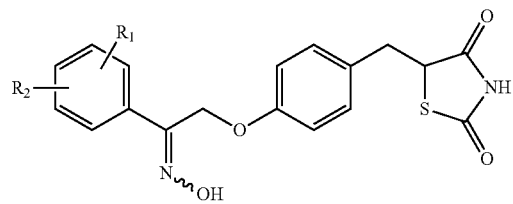

3A converting the compound of Formula 3A to a compound of Formula I.

2. The method of claim 1, further comprising converting a compound of Formula 4A

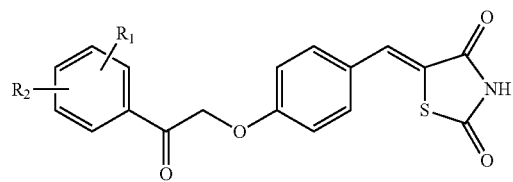

4A into a compound of Formula 2A.

3. The method of claim 2, further comprising treating the compound of Formula 4A with a reagent comprising $HONH_2 \cdot HCl$, $HONH_2$, TMSNHOTMS, $(H_2NOH)_2 \cdot H_2SO_4$, or any combination thereof to generate the compound of Formula 2A.

4. The method of claim 2, further comprising reacting a compound of Formula 5A

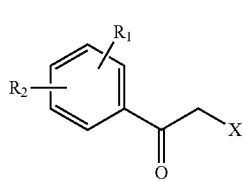

5A wherein X is a leaving group, with the compound of Formula 6A

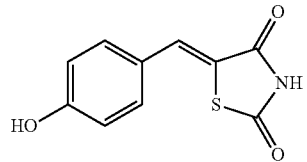

6A to form a compound of Formula 4A.

5. The method of claim 4, wherein X is a leaving group selected from —Br, —Cl, —I, —OMs, —OTs, —OTf, —OBs, —ONs, —O-tresylate, or —OPO(OR$_4$)$_2$, wherein each $R_4$ is independently $C_{1-4}$ alkyl or two of $R_4$ together with the oxygen and phosphorous atoms to which they are attached form a 5-7 membered ring.

6. The method of claim 4, wherein the compound of Formula 5A comprises

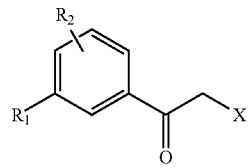

5A1 wherein $R_1$ is selected from a $C_{1-6}$ alkyl or $C_{1-6}$ alkoxy, either of which is optionally substituted with 1-3 halo, and $R_2$ is —H or halo.

7. The method of claim 4, wherein the compound of Formula 5A comprises

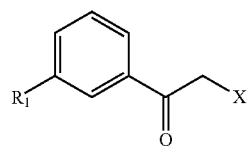

5A2 wherein $R_1$ is selected from a $C_{1-6}$ alkyl or $C_{1-6}$ alkoxy, either of which is optionally substituted with 1-3 halo.

8. The method of claim 4, wherein the compound of Formula 5A comprises

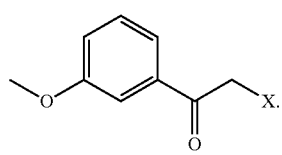

5A3

9. The method of claim 4, further comprising halogenating a compound of Formula 7A

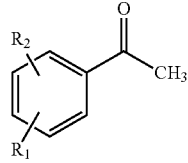      7A to form a compound of Formula 5A.

10. The method of claim 9, wherein $R_1$ is selected from a $C_{1-6}$ alkyl or $C_{1-6}$ alkoxy, either of which is optionally substituted with 1-3 halo, and $R_2$ is —H or halo.

11. The method of claim 10, wherein $R_1$ is $C_{1-6}$ alkoxy optionally substituted with 1-3 halo, and $R_2$ is —H.

12. The method of claim 4, wherein X is selected from —Br and —Cl.

13. The method of claim 4, further comprising reacting the compound

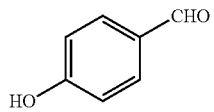

with the compound

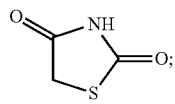

under condensation conditions to form a compound of Formula 6A.

14. The method of claim 1, wherein the compound of Formula 2A is reduced to a compound of Formula 3A in the presence of a reagent comprising $NaBH_4$, $LiBH_4$, $KBH_4$, or any combination thereof and a catalyst comprising $CoCl_2$.

15. The method of claim 1, wherein the compound of Formula 3A is converted to a compound of Formula I in the presence of an aqueous acid.

16. The method of claim 15, wherein the aqueous acid comprises aqueous HCl or aqueous $H_2SO_4$.

17. The method of claim 1, further comprising reacting a compound of Formula 5B

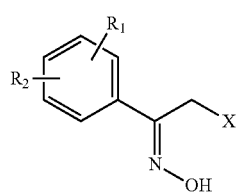     5B wherein X is a leaving group, with a compound of Formula 6A

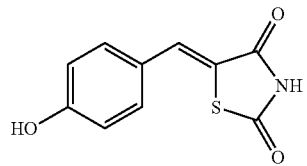     6A to form a compound of Formula 2A.

18. The method of claim 17, further comprising converting a compound of Formula 5A

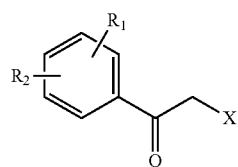     5A to form a compound of Formula 5B.

19. The method of claim 18, wherein the compound of Formula 5A comprises

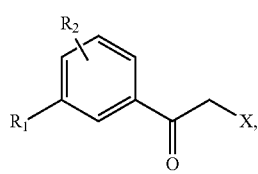

wherein $R_1$ is selected from a $C_{1-6}$ alkyl or $C_{1-6}$ alkoxy, either of which is optionally substituted with 1-3 halo, and $R_2$ is —H or halo.

20. The method of claim 19, wherein the compound of Formula 5A comprises

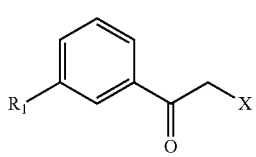     5A2 wherein $R_1$ is selected from a $C_{1-6}$ alkyl or $C_{1-6}$ alkoxy, either of which is optionally substituted with 1-3 halo.

21. The method of claim 20, wherein the compound of Formula 5A comprises

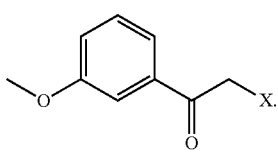     5A3

22. The method of claim 18, further comprising halogenating a compound of Formula 7A

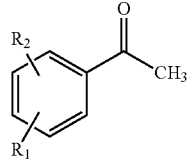

7A to form a compound of Formula 5A.

23. The method of claim 22, wherein $R_1$ is selected from a $C_{1-6}$ alkyl or $C_{1-6}$ alkoxy, either of which is optionally substituted with 1-3 halo, and $R_2$ is —H or halo.

24. The method of claim 23, wherein $R_1$ is selected from methoxy, ethoxy, or propoxy, any of which is optionally substituted with 1-3 halo.

25. The method of claim 17, wherein X is selected from —Br and —Cl.

26. The method of claim 25, further comprising reacting the compound

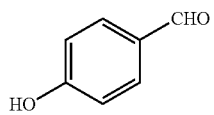

with the compound

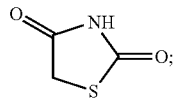

under condensation conditions to form a compound of Formula 6A.

27. The method of claim 17, wherein the compound of Formula 2A is reduced to a compound of Formula 3A in the presence of a reagent comprising $NaBH_4$, $LiBH_4$, $KBH_4$, or any combination thereof and a catalyst comprising $CoCl_2$.

28. The method of claim 27, wherein the compound of Formula 3A is converted to a compound of Formula I in the presence of an aqueous acid.

29. The method of claim 28, wherein the aqueous acid comprises aqueous HCl or aqueous $H_2SO_4$.

30. The method of claim 2, further comprising reacting a compound of Formula 8A

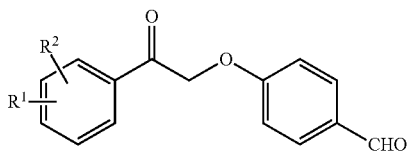

8A with the compound

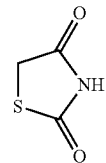

under condensation conditions to form a compound of Formula 4A.

31. The method of claim 30, further comprising reacting a compound of Formula 5A

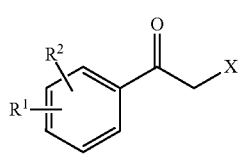

5A wherein X is a leaving group, with 4-hydroxybenzaldehyde to form a compound of Formula 8A.

32. The method of claim 31, wherein the compound of Formula 5A comprises

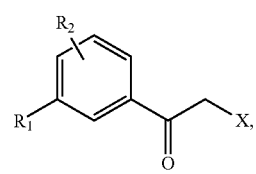

wherein $R_1$ is selected from a $C_{1-6}$ alkyl or $C_{1-6}$ alkoxy, either of which is optionally substituted with 1-3 halo, and $R_2$ is —H or halo.

33. The method of claim 32, wherein the compound of Formula 5A Comprises

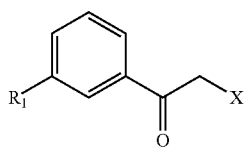

5A2 wherein $R_1$ is selected from a $C_{1-6}$ alkyl or $C_{1-6}$ alkoxy, either of which is optionally substituted with 1-3 halo.

34. The method of claim 33, wherein the compound of Formula 5A comprises

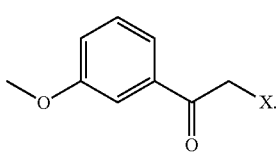

5A3

35. The method of claim 34, further comprising halogenating a compound of Formula 7A

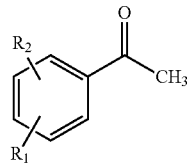

7A to form a compound of Formula 5A.

36. The method of claim 35, wherein $R_1$ is selected from a $C_{1-6}$ alkyl or $C_{1-6}$ alkoxy, either of which is optionally substituted with 1-3 halo, and $R_2$ is —H or halo.

37. The method of claim 36, wherein $R_1$ is selected from methoxy, ethoxy, or propoxy, any of which is optionally substituted with 1-3 halo.

38. The method of claim 31, wherein X is selected from —Br and —Cl.

39. The method of claim 1, further comprising reacting a compound of Formula 8B

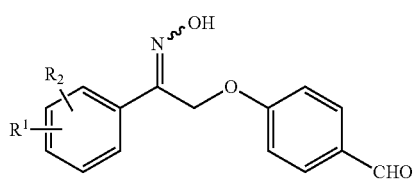

8B with the compound

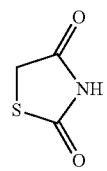

to generate the compound of Formula 2A.

40. The method of claim 39, further comprising reacting a compound of Formula 5B

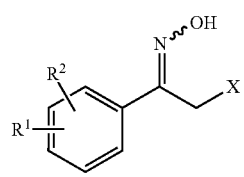

5B wherein X is a leaving group, with 4-hydroxybenzaldehyde to form a compound of Formula 8B.

41. The method of claim 40, wherein the compound of Formula 5B comprises

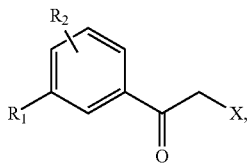

5 wherein $R_1$ is selected from a $C_{1-6}$ alkyl or $C_{1-6}$ alkoxy, either of which is optionally substituted with 1-3 halo, and $R_2$ is —H or halo.

42. The method of claim 41, wherein the compound of Formula 5B comprises

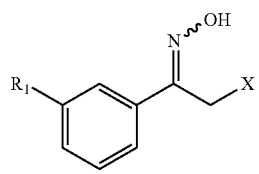

5B2 wherein $R_1$ is selected from a $C_{1-6}$ alkyl or $C_{1-6}$ alkoxy, either of which is optionally substituted with 1-3 halo.

43. The method of claim 41, wherein the compound of Formula 5B comprises

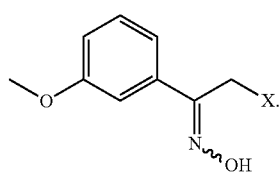

5B3

44. The method of claim 40, further comprising halogenating a compound of Formula 7B

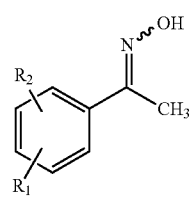

7B to form a compound of Formula 5B.

45. The method of claim 44, wherein $R_1$ is selected from a $C_{1-6}$ alkyl or $C_{1-6}$ alkoxy, either of which is optionally substituted with 1-3 halo, and $R_2$ is —H or halo.

46. The method of claim 45, wherein $R_1$ is selected from methoxy, ethoxy, or propoxy, any of which is optionally substituted with 1-3 halo.

47. The method of claim 43, wherein X is selected from —Br and —Cl.

* * * * *